(12) United States Patent
Walton, III

(10) Patent No.: US 8,308,062 B1
(45) Date of Patent: Nov. 13, 2012

(54) ELECTRONIC MEDICAL INFORMATION CARD AND SYSTEM AND METHOD OF USE

(76) Inventor: James F. Walton, III, Tallahassee, FL (US)

(*) Notice: Subject to any disclaimer, the term of this patent is extended or adjusted under 35 U.S.C. 154(b) by 9 days.

(21) Appl. No.: 13/114,773

(22) Filed: May 24, 2011

(51) Int. Cl.
*G06K 5/00* (2006.01)

(52) U.S. Cl. ...................................................... 235/380

(58) Field of Classification Search ........... 235/375–382
See application file for complete search history.

(56) References Cited

U.S. PATENT DOCUMENTS

| | | | |
|---|---|---|---|
| 5,658,016 A | 8/1997 | Goeken | |
| 5,793,882 A * | 8/1998 | Piatek et al. | 382/115 |
| 6,042,005 A * | 3/2000 | Basile et al. | 235/382 |
| D426,833 S | 6/2000 | Vanelli | |
| 6,140,936 A * | 10/2000 | Armstrong | 340/5.74 |
| 6,513,720 B1 | 2/2003 | Armstrong | |
| 6,580,356 B1 * | 6/2003 | Alt et al. | 340/5.8 |
| 6,651,892 B2 * | 11/2003 | Hooglander | 235/492 |
| 6,747,561 B1 | 6/2004 | Reeves | |
| 6,751,805 B1 * | 6/2004 | Austion | 2/94 |
| 6,845,063 B2 | 1/2005 | Mitchell | |
| 7,401,365 B2 * | 7/2008 | Neal et al. | 2/209.13 |
| 7,827,043 B2 | 11/2010 | Tahan | |
| 2002/0046061 A1 * | 4/2002 | Wright et al. | 705/3 |
| 2002/0097159 A1 * | 7/2002 | Hooglander | 340/573.1 |
| 2002/0120470 A1 | 8/2002 | Trice, Sr. | |
| 2003/0058110 A1 | 3/2003 | Rich | |
| 2003/0101077 A1 | 5/2003 | Whol | |
| 2003/0150143 A1 | 8/2003 | Hazard | |
| 2005/0194270 A1 | 9/2005 | Gombar | |
| 2006/0010012 A1 | 1/2006 | Franzblau et al. | |
| 2006/0015368 A1 | 1/2006 | Hockey | |
| 2006/0085226 A1 | 4/2006 | Kamber | |
| 2006/0142057 A1 | 6/2006 | Schuler et al. | |
| 2007/0158411 A1 | 7/2007 | Krieg, Jr. | |
| 2007/0265884 A1 | 11/2007 | Lubell et al. | |
| 2008/0016738 A1 * | 1/2008 | Talbott et al. | 40/633 |
| 2008/0126729 A1 | 5/2008 | Cai et al. | |
| 2008/0312962 A1 * | 12/2008 | Kirkwood | 705/2 |
| 2008/0319798 A1 | 12/2008 | Kelley | |
| 2009/0076849 A1 | 3/2009 | Diller | |
| 2009/0101721 A1 | 4/2009 | Hawthorne et al. | |
| 2009/0295569 A1 | 12/2009 | Corwin et al. | |
| 2010/0115609 A1 | 5/2010 | Spence | |

* cited by examiner

*Primary Examiner* — Thien M Le
*Assistant Examiner* — Christle Marshall
(74) *Attorney, Agent, or Firm* — The Livingston Firm; Edward M. Livingston, Esq.; Bryan L. Loeffler, Esq.

(57) ABSTRACT

An electronic medical information card (1) for storing an individual's emergency medical information on. The medical information card is stored in a storage sleeve (2) to attract the attention of medical personnel. The storage sleeve may be removably attachable to a user's driver's license, wallet, purse and so forth so that it may be easily seen by a first responder. In addition, the storage sleeve is water proof and fire resistant to protect the electronic medical information card from becoming damaged. The information on the electronic medical information card may be updated by an individual over the internet by sending updated information to a central location that updates the information in a central database and allows the user to download the updated information back onto the electronic medical information card.

14 Claims, 3 Drawing Sheets

ELECTRONIC MEDICAL INFORMATION CARD AND SYSTEM AND METHOD OF USE

BACKGROUND OF THE INVENTION

This invention relates to providing personal medical information to first responders during an emergency through the use of electronic storage devices and the internet.

During a medical emergency, time is of the essence for a patient to receive the proper care from first responders. In such instances it is important that first responders are aware of a patient's medical history including allergies to drugs, current medications and medical conditions. It also becomes necessary to have the patient's emergency contact information and physician contact information. In many instances patients are unconscious and unable to provide any information to first responders. Conventional methods of providing such information include medical identification bracelets which may list an individual's allergies or medical conditions. However, only a limited amount of information can be included on such bracelets. There have also been attempts to store an individual's medical information on electronic storage devices such as flash drives or radio frequency identification cards ("RFID") in the past. However, many of these devices are complicated to use and to store information on. In addition, many of these devices are carried in wallets or on key chains and can easily be missed by a first responder. In addition, such devices may be damaged in certain situations, such as if the devices become wet during a medical emergency involving water or if the devices are near flames. A further problem with conventional devices occurs if an individual is injured in a foreign country, thereby rendering the electronic storage device useless because the information stored on the device is not written in the first responder's native language.

Therefore, the need exists for a personal medical information card and system and method of use that allows a user to easily store medical information on the card, has a card that is easily identifiable by a first responder as being a medical information card, is protectable from water and fire and allows a foreign language speaking first responder to read the information stored on the card.

The relevant prior art includes the following references:

| Pat. No. (U.S. Patent References) | Inventor | Issue/Publication Date |
| --- | --- | --- |
| 7,827,043 | Tahan | Nov. 2, 2010 |
| 2010/0115609 | Spence | May 6, 2010 |
| 2009/0295569 | Corwin et al. | Dec. 3, 2009 |
| 2009/0101721 | Hawthorne et al. | Apr. 23, 2009 |
| 2009/0076849 | Diller | Mar. 19, 2009 |
| 2008/0126729 | Cai et al. | May 29, 2008 |
| 2008/0319798 | Kelley | Dec. 25, 2008 |
| 2007/0265884 | Lubell et al. | Nov. 15, 2007 |
| 2007/0158411 | Krieg, Jr. | Jul. 12, 2007 |
| 2006/0142057 | Schuler et al. | Jun. 29, 2006 |
| 2006/0085226 | Kamber | Apr. 20, 2006 |
| 2006/0015368 | Hockey | Jan. 19, 2006 |
| 2006/0010012 | Franzblau et al. | Jan. 12, 2006 |
| 2005/0194270 | Gombar | Sep. 8, 2005 |
| 6,845,063 | Mitchell | Jan. 18, 2005 |
| 6,751,805 | Austion | Jun. 22, 2004 |
| 6,747,561 | Reeves | Jun. 8, 2004 |
| 2003/0150143 | Hazard | Aug. 14, 2003 |
| 2003/0101077 | Whol | May 29, 2003 |
| 2003/0058110 | Rich | Mar. 27, 2003 |
| 6,513,720 | Armstrong | Feb. 4, 2003 |
| 2002/0120470 | Trice, Sr. | Aug. 29, 2002 |
| D426,833 | Vanelli | Jun. 20, 2000 |
| 5,658,016 | Goeken | Aug. 19, 1997 |
| 5,659,741 | Eberhardt | Aug. 19, 1997 |
| 5,337,290 | Ventimiglia et al. | Aug. 9, 1994 |
| 5,171,039 | Dusek | Dec. 15, 1992 |
| 4,575,127 | Michel | Mar. 11, 1986 |
| 4,491,725 | Pritchard | Jan. 1, 1985 |
| 4,318,554 | Anderson et al. | Mar. 9, 1982 |
| 3,792,542 | Cohan | Feb. 19, 1974 |

SUMMARY OF THE INVENTION

The primary object of the present invention is to provide an electronic medical information card and system and method of use that allows a user to easily store personal and medical information on the card.

Another object of the present invention is to provide an electronic medical information card that is easily identifiable by a first responder as being a medical information card.

An additional object of the present invention is to provide an electronic medical information card and system and method of use that protectable from water and fire.

The present invention fulfills the above and other objects by providing an electronic medical information card for storing emergency medical information, such as blood type, allergies, medical conditions, present medications, age, doctor information and emergency contact information. The card is preferably a secure digital ("SD") card or other electronic smart card having an electronic storage means. The card is stored in a brightly colored storage sleeve to attract the attention of medical personnel. The sleeve is removably attachable to a user's driver's license, wallet, purse and so forth so that it may be easily seen by a first responder. In addition, the storage sleeve is water proof and fire resistant to protect the electronic medical information card from becoming damaged. The information on the electronic medical information card may be updated by an individual over the internet by sending updated information to a central location that updates the information in a central database and allows the user to download the updated information back onto the electronic medical information card. An additional feature of the card allows a first responder to translate the information stored on the electronic medical information card into the first responder's native language.

The above and other objects, features and advantages of the present invention should become even more readily apparent to those skilled in the art upon a reading of the following detailed description in conjunction with the drawings wherein there is shown and described illustrative embodiments of the invention.

BRIEF DESCRIPTION OF THE DRAWINGS

In the following detailed description, reference will be made to the attached drawings in which.

Figure 1:
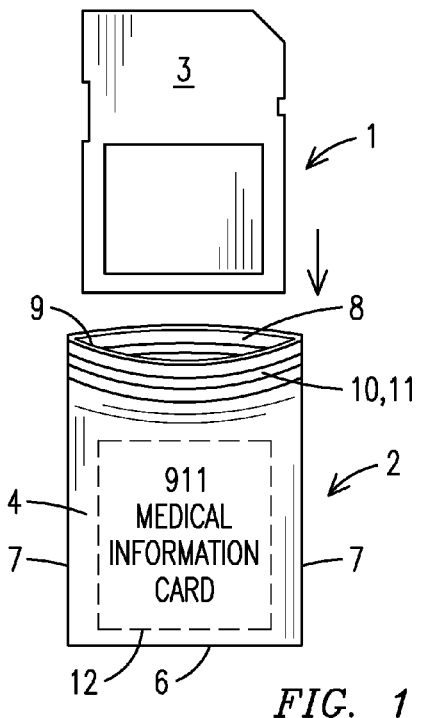
FIG. 1 is a front view of an electronic medical information card and storage sleeve of the present invention.

DESCRIPTION OF THE PREFERRED
EMBODIMENTS

For purposes of describing the preferred embodiment, the terminology used in reference to the numbered accessories in the drawings is as follows:

| | |
|---|---|
| 1. | medical identification card |
| 2. | storage sleeve |
| 3. | secure digital ("SD") card |
| 4. | front panel |
| 5. | rear panel |
| 6. | bottom edge |
| 7. | side edge |
| 8. | opening |
| 9. | top edge |
| 10. | sealing means |
| 11. | adhesive |
| 12. | label portion |
| 13. | attachment means |
| 14. | adhesive |
| 15. | individual visits the service provider's website |
| 16. | individual provides the service provider with contact information |
| 17. | service provider reviews the contact information |
| 18. | information is determined to not be accurate or to be invalid |
| 19. | account is denied |
| 20. | information is determined to be accurate and valid |
| 21. | individual is provided with a username and password |
| 22. | individual is sent package |
| 23. | individual logs into his or her account |
| 24. | individual enters medical information |
| 25. | medications |
| 26. | emergency contacts |
| 27. | medical conditions |
| 28. | allergies |
| 29. | physician contact information |
| 30. | family history information |
| 31. | information is then stored in the individual's personal account on a central database |
| 32. | medical information is downloaded the medical information card |
| 33. | store medical information card and attach storage sleeve |
| 34. | first responder responds to a medical emergency |
| 35. | first responder locates the medical information card |
| 36. | first responder places the medical information card into an electronic device |
| 37. | medical information is opened |
| 38. | convert text of the medical information to a foreign language |
| 39. | first responder provided with a contact telephone number |
| 40. | first responder calls service provider |
| 41. | service provider contacts individual's emergency contacts |

Figure 2:
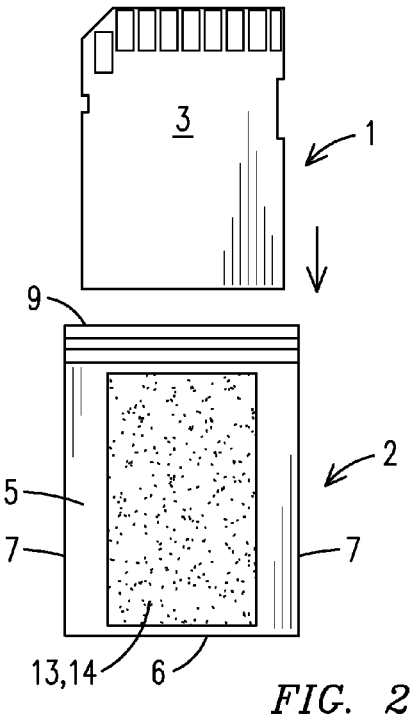
FIG. 2 is a rear view of an electronic medical information card and storage sleeve of the present invention.

With reference to FIGS. 1 and 2, a front view and a rear view, respectively, of an electronic medical information card 1 and storage sleeve 2 of the present invention is shown. The electronic medical information card 1 allows an individual to store emergency medical information, such as blood type, allergies, medical conditions, present medications, age, doctor information and emergency contact information. The medical information card is preferably a secure digital ("SD") card 3 or other electronic smart card having an electronic storage means, such as a radio-frequency identification ("RFID") chip. The medical information card 1 is stored in a storage sleeve 2 comprising a front panel 4 attached to a rear panel 5 along a bottom edge 6, and two side edges 7. An opening 8 is locate along a top edge 9 of the storage sleeve 2 for inserting the electronic 4 medical information card 1 through. A sealing means 10, such as adhesive 11, zip lock and so forth, is located along the opening 8 to seal the storage sleeve 2 shut. The storage sleeve 2 is preferably brightly colored to attract the attention of medical personnel and has a label portion 12 that informs a first responder that a medical information card 1 is inside the storage sleeve 2. The storage sleeve 2 may be removably attachable via an attachment means 13, such as an adhesive 14, to a user's driver's license, wallet, purse and so forth so that it may be easily seen by a first responder when a first responder goes to retrieve a patients driver's license. In addition, the storage sleeve 2 is preferably water proof and fire resistant to protect the medical information card 1 from becoming damaged if a patient is exposed to water and/or fire.

Figure 3:
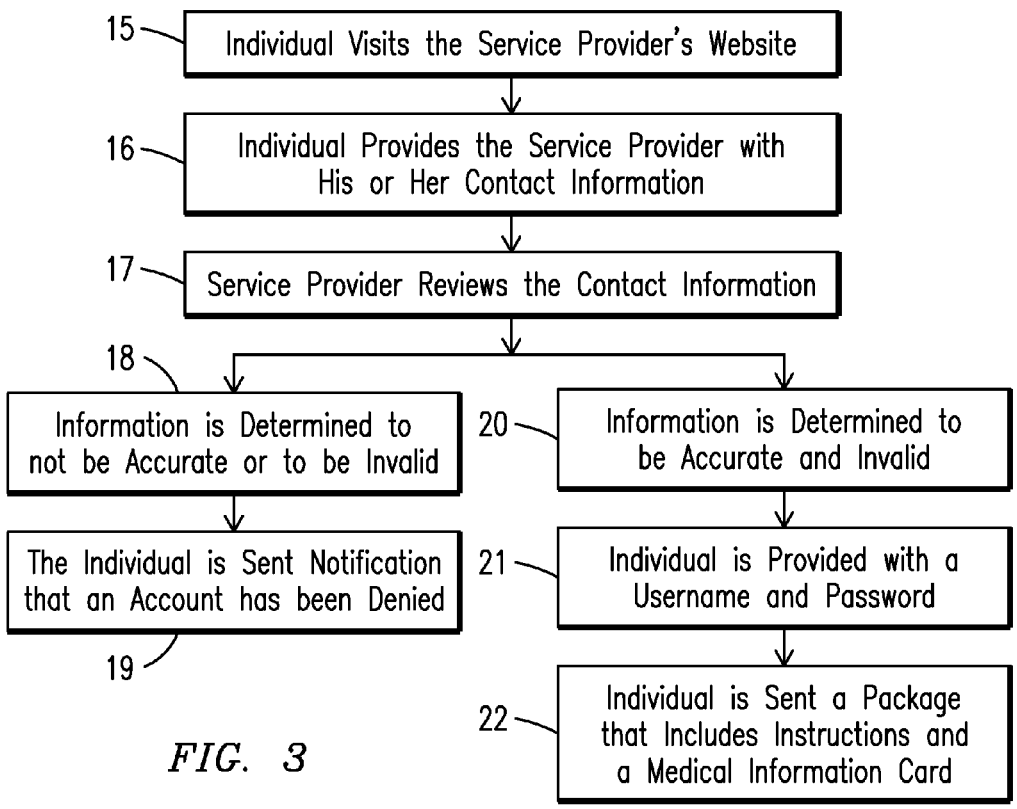
FIG. 3 is a flow chart showing an individual signing up for an account with a service provider that provides a medical information card to the individual.

With reference to FIG. 3, a flow chart showing an individual signing up for an account with a service provider that provides a medical information card to the individual. First, the individual visits the service provider's website 15. Then, the individual provides the service provider with his or her contact information, which includes the individual's name, address, phone number, email address and so forth 16. The service provider then reviews the contact information to determine the accuracy of the information and the validity of the information 17. If the information is determined to not be accurate or to be invalid 18, then the individual is sent notification, preferably via email, that an account has been denied 19. If the information is determined to be accurate and valid 20, then the individual is sent an approval, preferably via email, that an account has been created and the individual is provided with a username and password 21. Next, the individual is sent a package that includes instructions and a medical information card 22.

Figure 4:
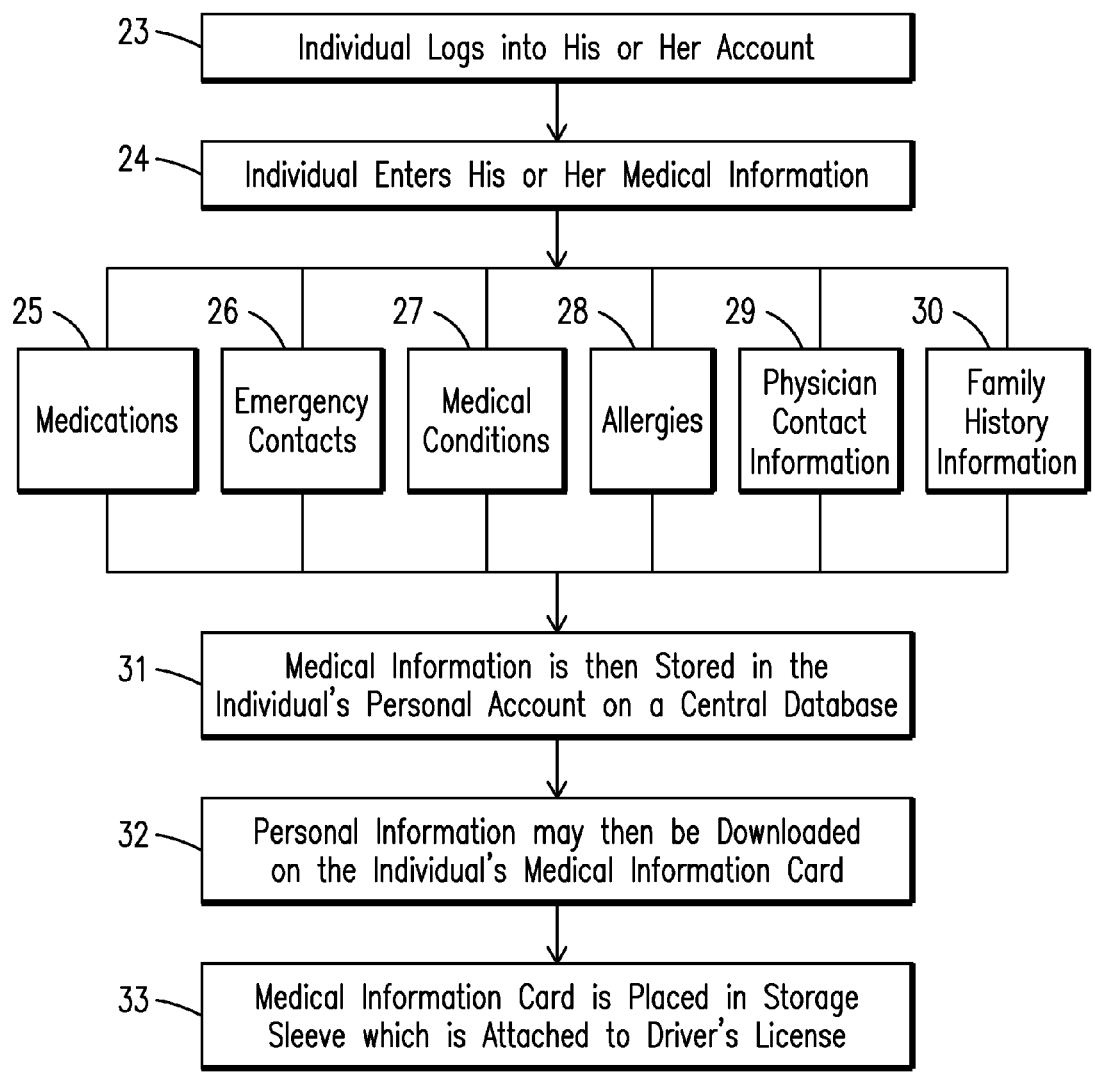
FIG. 4 is a flow chart showing the system and method of the present invention in which an individual enters medical information into an online account.

With reference to FIG. 4, a flow chart showing the system and method of the present invention in which an individual enters medical information into an online account is shown. First, the individual logs into his or her account using the username and password provided by the service provider 23. Then, the individual enters his or her medical information 24, which includes medications 25, emergency contacts 26, medical conditions 27, allergies 28, physician contact information 29, family history information 30 and so forth. The medical information is then stored in the individual's personal account on a central database 31. The medical information may then be downloaded on the individual's medical information card 32 by downloading a zip file, which may be encrypted, containing the medical information and copying it onto the medical information card. The individual may then attach a storage sleeve to his or her license, wallet, purse and so forth, insert the medical information card into the storage sleeve and seal the storage sleeve 33.

Figure 5:
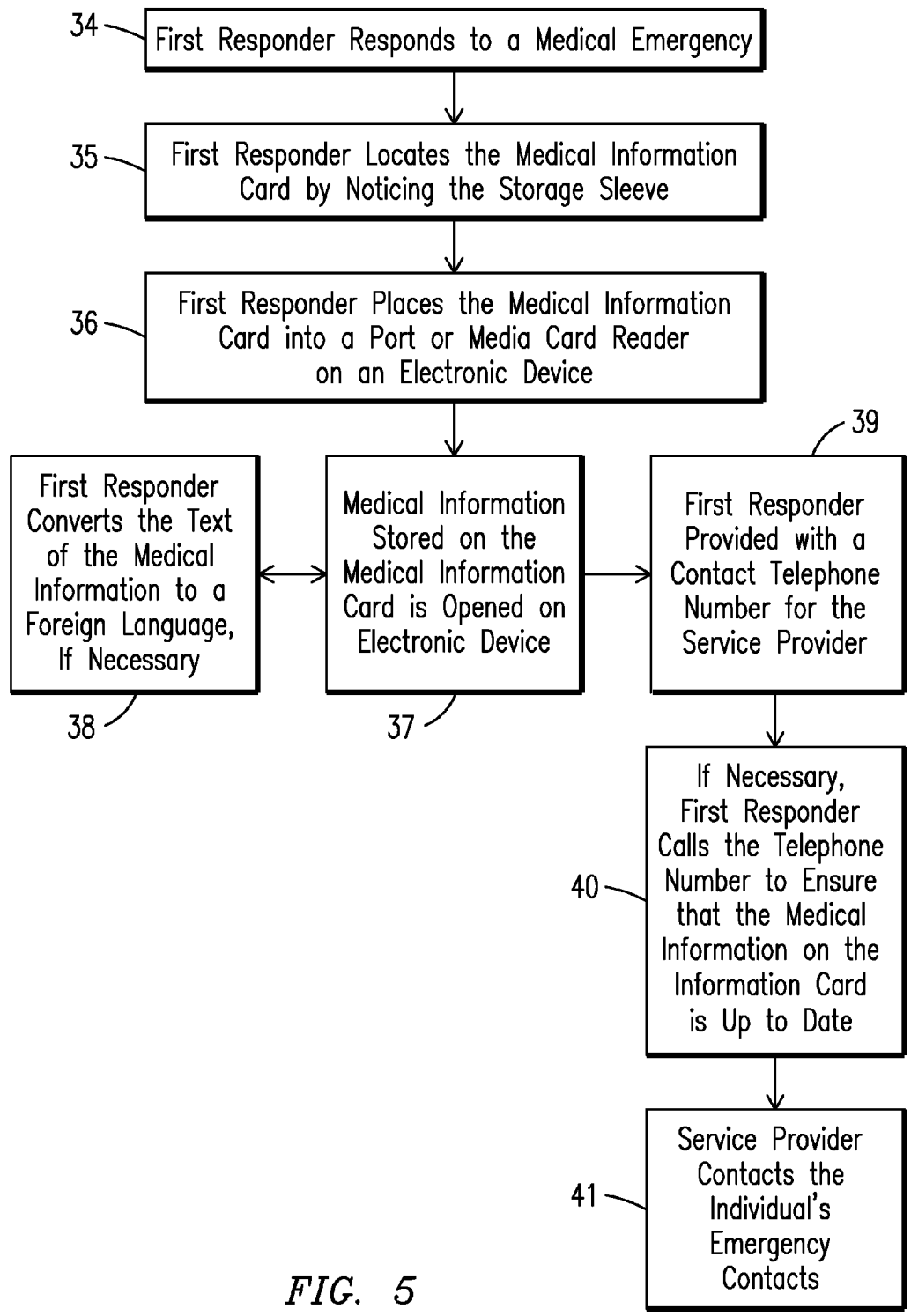
FIG. 5 is a flow chart showing the system and method of the present invention in which a first responder retrieves medical information from a patient's medical information card.

Finally with reference to FIG. 5, a flowchart showing the system and method of the present invention in which a first responder retrieves medical information from a patient's medical information card is shown. First, a first responder responds to a medical emergency 34. Then, the first responder locates the medical information card by noticing the storage sleeve 35. Next, the first responder places the medical information card into a port or media card reader on an electronic device, such as a laptop or tablet 36. Then, the medical information stored on the medical information card is opened and the first responder may read and/or print the medical information 37. The first responder may also convert the text of the medical information to a foreign language if the patient has been injured in a foreign country 38. The first responder will also be provided with a contact telephone number for the service provider 39. In addition, the service provider will be able to tell when the information on the card was last updated. The first responder may call the telephone number if necessary to ensure that the medical information on the medical information card is up to date with the most current medical information stored on the central data base 40. In addition, after being notified of a medical emergency the service provider will contact the individual's emergency contacts to inform them of the medical emergency 41.

It is to be understood that while a preferred embodiment of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

Having thus described my invention, I claim:

1. A method for using a medical information card for storing medical information and providing medical information to first responders comprising the steps of:
   a. an individual creating an account with a service provider over the internet;
   b. the service provider providing a medical information card to the individual;
   c. the individual providing his or her medical information to the service provider to be saved in a central database;
   d. the individual downloading the medical information from the central database and storing the medical information on the medical information card;
   e. the individual providing the service provider with his or her contact information; and
   f. the service provider reviewing the contact information and rendering a decision on whether to allow the individual to have an account.

2. The method of claim 1 further comprising a step after step d of:
   sealing the medical information card in a storage sleeve and attaching the storage sleeve to a surface where it will be easily found by a first responder.

3. The method of claim 1 further comprising steps of:
   the service provider deciding to allow the individual to have an account;
   the service provider creating an account and providing the individual with a username and password; and
   the service provider providing a medical information card to the individual.

4. The method of claim 2 further comprising steps of:
   a first responder locating the storage sleeve and medical information card during an emergency; and
   the first responder reading the medical information stored on the medical information card using an electronic device.

5. The method of claim 4 further comprising a step of:
   the first responder translating the medical information to a foreign language using software stored on the medical information card.

6. The method of claim 4 further comprising steps of:
   the first responder being provided a contact number for contacting the service provider; and
   the first responder contacting the service provider.

7. The method of claim 6 further comprising a step of:
   the service provider contacting emergency contacts on the behalf of the individual.

8. A system for using a medical information card for storing medical information and providing medical information to first responders comprising:
   an individual creating an account with a service provider over the internet;
   the service provider providing a medical information card to the individual;
   the individual providing his or her medical information to the service provider to be saved in a central database;
   the individual downloading the medical information from the central database and storing the medical information on the medical information card;
   the individual providing the service provider with his or her contact information; and
   the service provider reviewing the contact information and rendering a decision on whether to allow the individual to have an account.

9. The system of claim 8 further comprising:
   sealing the medical information card in a storage sleeve and attaching the storage sleeve to a surface where it will be easily found by a first responder.

10. The system of claim 8 further comprising:
    the service provider deciding to allow the individual to have an account;
    the service provider creating an account and providing the individual with a username and password; and
    the service provider providing a medical information card to the individual.

11. The system of claim 9 further comprising:
    a first responder locating the storage sleeve and medical information card during an emergency; and
    the first responder reading the medical information stored on the medical information card using an electronic device.

12. The system of claim 11 further comprising:
    the first responder translating the medical information to a foreign language using software stored on the medical information card.

13. The system of claim 11 further comprising:
    the first responder being provided a contact number for contacting the service provider; and
    the first responder contacting the service provider.

14. The system of claim 13 further comprising:
    the service provider contacting emergency contacts on the behalf of the individual.

* * * * *